United States Patent
Olson

Patent Number: 5,433,204
Date of Patent: Jul. 18, 1995

[54] METHOD OF ASSESSING PLACENTATION

[75] Inventor: Camilla Olson, 4143 Hubbartt Dr., Palo Alto, Calif. 94306

[73] Assignee: Camilla Olson, Palo Alto, Calif.

[21] Appl. No.: 152,168

[22] Filed: Nov. 16, 1993

[51] Int. Cl.$^6$ ............................................. A61B 8/06
[52] U.S. Cl. ........................... 128/661.08; 128/662.02
[58] Field of Search ............. 128/662.02, 661.07–661.1; 424/9

[56] References Cited

U.S. PATENT DOCUMENTS

| | | | |
|---|---|---|---|
| 3,732,532 | 5/1973 | Flaherty et al. | 128/661.07 |
| 4,024,084 | 6/1977 | Soldner | 128/760 |
| 4,094,965 | 6/1978 | Layne et al. | 424/1.5 |
| 4,293,537 | 10/1981 | Wong | 424/1 |
| 4,442,843 | 4/1984 | Rasor et al. | 128/662.02 |
| 4,681,119 | 7/1987 | Rasor et al. | |
| 5,205,287 | 4/1993 | Erbel et al. | |
| 5,209,720 | 5/1993 | Unger | |
| 5,228,446 | 7/1993 | Unger | |
| 5,230,343 | 7/1993 | Guberek et al. | 128/666 X |
| 5,230,882 | 7/1993 | Unger | |
| 5,285,788 | 2/1994 | Arenson et al. | 128/660.05 |

FOREIGN PATENT DOCUMENTS 1323082 7/1987 U.S.S.R. .

OTHER PUBLICATIONS

Finberg, *Definitive Prenatal Diagnosis of Monoamniotic Twins: Swallowed Amniotic Contrast Agent Detected in Both Twins on Sonographically Selected CT Images,* J. Ultrasound Med. 10:513–16 (1991).

Panigel et al., *Magnetic Resonance Imaging (MRI) of the Placental Circulation Using Gadolinium-DTPA as a Paramagnetic Marker in the Rhesus Monkey in Vivo and the Perfused Human Placenta in Vitro,* Trophoblast Research 3:271–82 (Kaufmann et al. ed. 1988).

Panigel et al., *Magnetic Resonance Imaging of the Placenta in Rhesus Monkeys, Macaca mulatta,* J. Med. Perinatol. 17:3–18 (1988).

Mattrey, *Ultrasound Contrast Media: Sonographic Enhancement of Doppler Signals and Perfused Tissues with Perfluorooctylbromide,* Invest. Radiol. 25:S158–59 (1990), followed by Discussion at S167.

Schlief et al., *Saccharide-based Ultrasound Contrast Media: Basic Characteristics and Results of Clinical Trials, New Dimensions of Contrast Media,* Proc. of Second Internatl. Sympos. on Contrast Media, Osaka, Japan, 141–46 (Katayama et al. ed. 1990).

Schlief et al., *Hysterosalpingo-Contrast Sonography of the Uterus and Fallopian Tubes: Results of a Clinical Trial of a New Contrast Medium in 120 Patients,* Radiology 178:213–15 (1991).

Andre et al., *Enhancement of the Echogenicity of Flowing Blood by the Contrast Agent Perflubron,* Invest. Radiol. 28:502–506 (1993).

*Primary Examiner*—Francis Jaworski
*Attorney, Agent, or Firm*—Morrison & Foerster

[57] ABSTRACT

An improved method of visualizing blood flow in the maternal placenta is provided. By utilizing contrast media to enhance the ultrasound image, the condition of the maternal placenta during pregnancy can be evaluated so as to permit intervention for correcting abnormal conditions of such blood flow, if required.

14 Claims, 1 Drawing Sheet

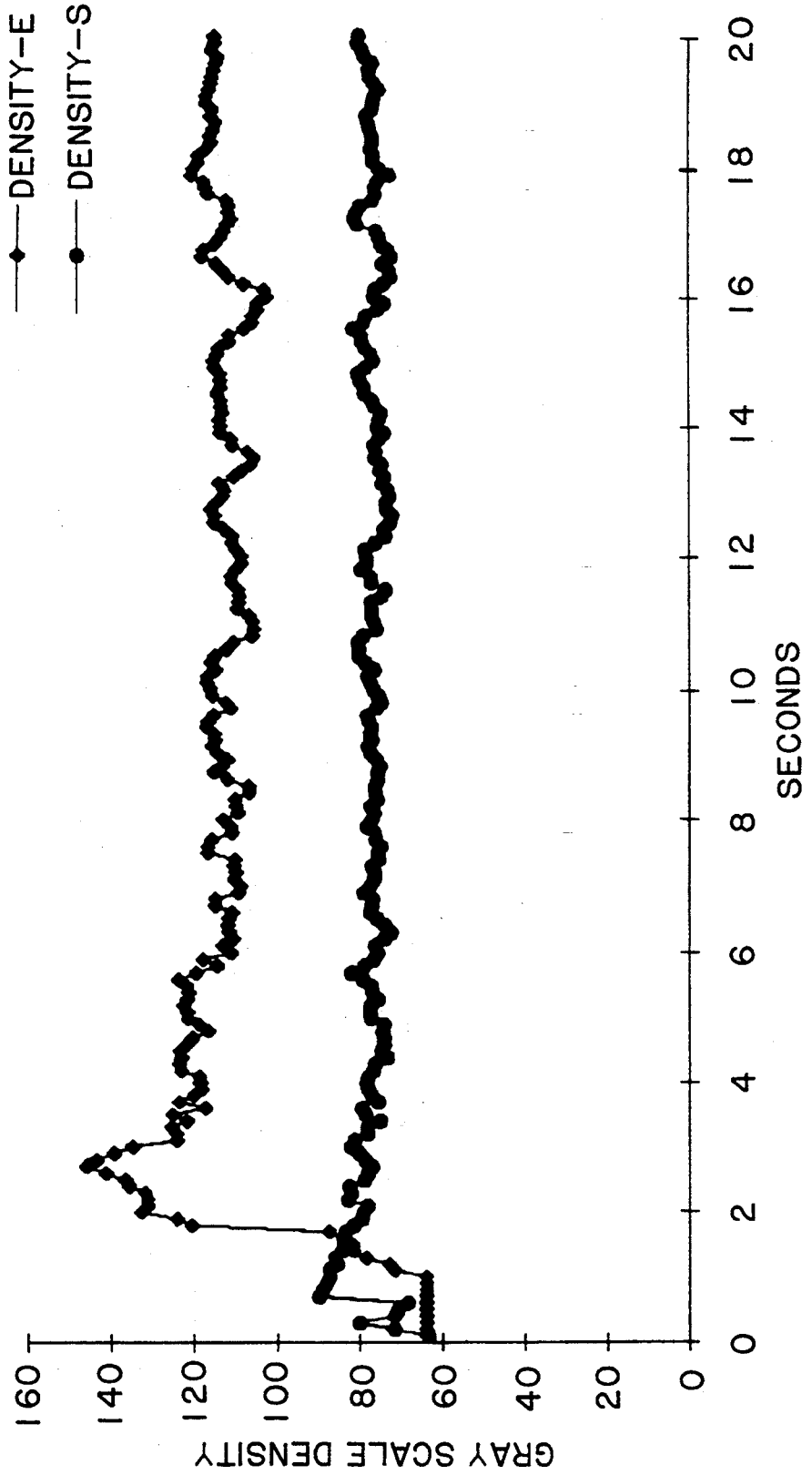

METHOD OF ASSESSING PLACENTATION

FIELD OF THE INVENTION

The present invention relates to the assessment of placental function in as early as the second trimester of pregnancy. In particular, the invention relates to the use of contrast media to enhance the ultrasound detection of blood flow in a placenta during pregnancy.

BACKGROUND ART

The placenta is a remarkable fetal support system. It functions as the fetal lung and is responsible for all gas transfer from the mother to the fetus. The placenta controls excretory functions, water balance, and pH regulation as the fetal kidney. It acts as the fetal gut by performing catabolic and resorptive functions. It also performs most synthetic and secretory functions of the endocrine glands and liver. Finally, the placenta provides hematopoiesis of the bone marrow during the early stages of pregnancy, controls heat transfer of the skin, and performs immunological functions to a largely unknown degree.

Disruptions in the maternal circulation to the placenta, and thus in the fetal circulation, can result in intrauterine growth retardation ("IUGR") or even fetal death. IUGR may be a direct effect of hypoxia upon fetal tissues or caused by a reduction in the supply of nutrients to the fetus. The importance of uteroplacental blood flow in the nutrition of both the maternal and fetal placenta has been shown by observations of placentas in animal models and in fetuses that have not survived IUGR. Histological characteristics used by investigators to describe placental insufficiency have been correlated to the consequences of fetal nutritional deprivation.

As many as 250,000 babies are born each year that weigh less than 2,500 grams and are thus described as low birth weight (LBW) infants. These babies are 40 times more likely to die in the neonatal period. For the segment of newborns weighing less than 1,500 grams, the relative risk is 200 times greater. In 1990, the hospital-related costs of caring for all LBW infants during the neonatal period totaled more than two billion dollars. LBW infants make up only about 7% of all births, but the costs associated with their care in 1990 represented about 57% of the costs incurred for all newborns.

Even when LBW infants survive, about half are categorized as "small for their gestational age" ("SGA"). These SGA infants are significantly compromised in utero and lack the resilience normally seen for infants at their gestational age during labor, delivery and the neonatal period. Sometimes, infants are even classified as both premature and SGA, and these babies constitute a significant minority that have an even higher morbidity rate. Epidemiological studies have shown that it is the relative weight of the infant, rather than the length of gestation, that is the primary factor affecting an infant's chances of survival.

Additionally, pathological alterations in the placental vasculature have been correlated to preeclampsia, a disease affecting 5 to 10% of pregnant women. Left undetected, women with preeclampsia are at risk for maternal death, fetal IUGR and fetal death.

There has been a need to reduce perinatal morbidity and mortality by significantly reducing the incidence of both the SGA fetus and the LBW fetus. To this end, there is a need to protect human fetuses that are at risk by assuring a maternal environment that can support fetal nutritional needs.

One way to do this is to attempt to visualize the maternal circulation in the placenta in a sonogram. However, current methods that employ ultrasound techniques including Doppler flow to examine intervillous blood flow of the mother's circulation in the placenta have not been entirely successful. This is because current ultrasound techniques are limited by the low flow state, the relatively small target spaces, and the lack of spatial resolution.

Contrast media have been suggested to detect aspects of flow and tissue perfusion in other situations, most frequently, the heart or the organs of the gastrointestinal tract, but also including the cardiovascular system, liver, spleen, kidney, pancreas, tumor tissue, muscle tissue, or bodily fluids such as blood. See, for example, Unger, U.S. Pat. No. 5,209,720 issued May 11, 1993 (tumor tissue, muscle tissue or blood fluid), and Unger et al., U.S. Pat. No. 5,228,446 issued Jul. 20, 1993 (liver, spleen, kidneys, heart, vasculature, diseased tissue and blood flow).

More specifically, Erbel et al., U.S. Pat. No. 5,205,287 issued 27 Apr. 1993, states that certain ultrasonic contrast media can be used to visualize the blood flow in the right ventricle or left side of the heart, the myocardium, the liver, spleen, kidney or brain. Further, the contrast media of Erbel et al. are described as also suitable for the visualization of the urinary bladder, ureter, uterus or vagina. Two U.S. patents (Rasor et al. U.S. Pat. No. 4,442,843 and Rasor et al., U.S. Pat. No. 4,681,119) describe the use of contrast media to enhance ultrasonic images of a number of liquid-filled regions of the body, such as those of the reproductive system.

Others have disclosed the use of an intrauterine catheter containing a contrast medium in conjunction with a diagnostic scanning device. For example, Eden, U.S. Pat. No. 4,349,033 issued Sep. 14, 1982, discloses a method of providing a fluid to the interior of a body cavity, such as woman's uterus, while scanning with an ultrasonic transducer. Visualization of pelvic structures, the Fallopian tubes, ovaries and the cul-de-sac is said to be improved. The technique is described as allowing a doctor to detect the presence of a pelvic mass, abnormal vaginal bleeding, pelvic cancer staging, congenital anomalies or pelvic infections.

Two investigators have described the use of an ultrasound contrast medium to evaluate the condition of Fallopian tubes. Unger, U.S. Pat. No. 5,230,882 issued Jul. 27, 1993, discloses a general method for imaging a patent using ultrasound comprising administering to the patient a liposome contrast medium and scanning the patient using an ultrasound device. In a nonvascular application, the liposomal contrast medium may be injected directly into the area to be scanned, such as into the uterine cavity to assess "patency" of the Fallopian tubes. According to the second investigator, in the second document, Soviet Union Patent Document No. 1323082, published Jul. 15, 1987, "uterine tube patency" may be diagnosed by filling the tubes with a spasmolytic solution, followed by ultrasound visualization. However, there is no disclosure of using ultrasound during pregnancy, let alone a teaching of applicability to the placenta.

As to the use of an ultrasound contrast medium during pregnancy for other purposes, Finberg et al., in an article entitled "Definitive Prenatal Diagnosis of Monoamniotic Twins: Swallowed Amniotic Contrast Agent Detected in Both Twins on Sonographically Selected CT Images", *J Ultrasound Med* (1991) 10:513-16, describes the diagnosis of the potentially dangerous condition of monoamniotic twinning at 27 weeks. This diagnosis was by the detection, on sonographically selected computed tomographic ("CT") images, of intestinal opacification in each twin after a single injection of the contrast medium into the amniotic space. FIGURE 1 of the publication, which appears to be a conventional sonogram without the use of contrast media, is described as showing the positions where the umbilical cords of both twins insert into the placenta and the absence of a detectable intervening amniotic membrane. When a single amniocentesis is performed to inject a contrast medium into the amniotic fluid, which is then swallowed by each twin, the ultrasound-selected CT images showed concentrated contrast medium in the intestine of each twin, confirming that they were monoamniotic. When this condition was confirmed, labor was induced to deliver the twins prematurely to prevent catastrophic events due to the knotting of intertwined loops of the two umbilical cords sharing the same amniotic sac.

However, there is no teaching in Finberg et al. of how to evaluate the condition of the placenta itself, or the volume of blood flowing through the placenta, even in this environment, much less in instances of apparently normal pregnancies.

The literature in this area can thus be divided roughly into two groups: (1) the use of ultrasound contrast media to assess the condition of various body cavities, such as parts of the reproductive system, for example, the uterus, Fallopian tubes and/or vagina; (2) and the use of ultrasound scanning with a contrast medium during pregnancy to confirm a suspected diagnosis of monoamniotic twins.

Moreover, those working in the art have not proposed the use of contrast media to facilitate the ultrasound assessment of the condition of the placenta itself during pregnancy. The use of contrast media for direct observation of the fetus has generally been ruled out as involving an undue risk, particularly in monitoring what is an apparently healthy pregnancy. Those working in the ultrasound art have expressly avoided fetal-prenatal vascular studies altogether due to the prevailing fears of introducing complications during pregnancy.

Therefore, there remains a need for a method to study maternal intervillous and related placental blood flow that allows for a measure of uteroplacental circulation. In this way, it is proposed that poor placentation can be detected at a sufficiently early stage to attempt treatment.

DISCLOSURE OF THE INVENTION

It has now been discovered that contrast media can be used to enhance the ultrasound detection of blood flow in a placenta during the pregnancy of an animal. Specifically, abnormalities in the placenta of a pregnant, female animal may be detected by a method for evaluating blood flow in the placenta comprising the steps of:
a. administering to the animal an efficacious amount of a contrast medium; and
b. scanning the abdomen of the animal with the transducer of an ultrasound scanner; and
c. assessing the condition of the placenta by evaluating the scan.

The use of ultrasound contrast media allows greater backscatter and thus augments the ability of current ultrasound techniques to image the blood flow found in the intervillous space of an animal's placenta. Further, when ultrasound sonograms are enhanced by the use of appropriate contrast media, abnormalities can be detected early enough for therapeutic intervention, resulting in a lower perinatal morbidity and mortality rate.

BRIEF DESCRIPTION OF DRAWINGS

The present invention will be more clearly understood by referring to the following drawings, in which:
FIGURE 1 illustrates the change in intensity versus time for two different compositions.

MODES OF CARRYING OUT THE INVENTION

The method of the invention is applicable to any animal that is a "placental" - - - i.e., that nurtures the unborn fetus through a placenta. Such animals include humans, other primates, mammalian food animals and pets.

One purpose of the invention is to allow the measurement of maternal blood flow of such animals into the intervillous space. It is the maternal blood in the intervillous space that constantly bathes the fetal villi, and it is through the fetal villi that nutrients are delivered into fetal circulation.

From the mother's heart descends the aorta, and the terminal branches of the aorta are the common iliac arteries. Arising opposite the fourth lumbar vertebrae, they pass downward and laterally to end at the lumbosacral junction by dividing into internal and external iliac arteries. The internal iliac arteries descend into the pelvis and give off the uterine artery, which supplies the uterus and separates into arcuate arteries. Each arcuate artery subdivides hundreds of times into tiny spiral arteries. These very small arteries feed into the intervillous space. It is this blood flow from the mother's arcuate arteries into the spiral arteries and into the intervillous space that provides important information regarding the nutritional condition of the fetus.

Postpartum to an IUGR pregnancy, analysis of the placenta in a pathology lab typically reveals signs of pathology along the spiral arteries, which tend to hinder or even obstruct the blood flowing from the mother's spiral arteries into the intervillous space. Usually, the spiral arteries are significantly narrowed or hardened and may even become completely clogged.

Using conventional ultrasound techniques, the blood flow in the spiral arteries cannot be visualized because it is simply too small and there are literally hundreds of them, such that examining each one of them independently would be out of the question. Thus, it would not be possible, let alone practical, to attempt to sample each and every spiral artery to determine whether or not blood is flowing freely through it.

While those in the art have long desired the ability to visualize or measure the blood flow into the intervillous space, the problem has been that blood flow, even in normal placentation, is too slow to achieve acceptable resolution in conventional Doppler sonography. Occasionally, particularly talented sonographers may have been able to get a fleeting visible image, but such an image has not been produced reproducibly.

In the claimed invention, the use of an appropriate contrast medium allows visualization of the rate and direction of blood flow in the arcuate arteries, spiral arteries and intervillous space by Doppler ultrasound examination. A contrast medium is administered appropriately, such as, for example, by injection into one of the mother's veins or arteries. The Doppler transducer is fixed on the mother's abdomen and focused on the desired location related to the placenta, such as intervillous space. The gain of the transducer is then changed to produce a low intensity signal, so that very little motion or activity is seen on the visual display, such as a CRT or liquid crystal screen.

When the contrast medium is introduced, the flushing of the medium through the placenta can be observed as a lighting up of the intervillous space, somewhat like a flare or firecracker. This flare phenomenon is called a "bloom." Then the bloom caused by the medium fades away as the medium is washed out of the region.

An important element in an ultrasound system is the scanner transducer. The transducer converts electrical to mechanical energy and vice versa. An ultrasound scanner, under computer control, sends a short pulse of electricity to the transducer to generate a burst of mechanical vibrations (sound waves). The sound generated has a frequency above the audible limit of 20 kHz and, in clinical applications, is usually in the range of 2 to 10 MHz. The frequency of the sound waves is adjusted to accommodate the contrast medium used, as is generally understood in the art.

The burst of sound travels down the tissue and reflects back. When the reflected wave strikes the now silent transducer, the resulting mechanical energy is converted back to electrical energy, which is then returned to the computer. The time delay between the moment the sound was generated and the moment a signal was received allows the computer to place a dot on the visual display. The brightness of the dot is related to the amplitude of the received signal. The computer keeps track of the position of the transducer (or sound beam) and its angle. The dot is positioned along the long axis of the transducer at a point dictated by the time delay.

Reflection of sound in biological tissues occurs when the sound beam strikes an interface separating two regions with different acoustic impedance (the product of mass density and acoustic velocity). Since the difference in density between most tissues is minimal, the major contributor to the differences is velocity. The difference in velocity between most animal tissues is on the order of about 1 to 5%.

Surfaces of organs typically reflect sound in a manner analogous to the reflection of light off the surface of a mirror. However, when the sound beam strikes a series of smaller, more diffuse reflectors, it is scattered in nearly all directions in a manner analogous to light reflected from a series of small spheres. Particles of ultrasound contrast media are considered diffuse reflectors or scatterers.

Overall tissue texture is dependent upon the number of scatterers present in the field and the spatial relationship among them. The image is the final result of interactions between the sound wave and the scatterers that interfere with each other in a constructive or a destructive manner.

The Doppler ultrasound effect is produced when the reflective surface is in motion relative to the transducer, for example, a flow of blood through a blood vessel or highly vascular tissues. If the reflective tissue is approaching the transducer, the sound waves are intercepted at a faster rate than if the reflective tissue were stationary, increasing the frequency of the reflected sound. Conversely, if the reflective tissue is moving away from the transducer, it would intercept the waves at slower rate, and the reflected sound will have a lower frequency.

By evaluating the difference between the frequency delivered by the transducer and the frequency received, the velocity of the reflective tissue in the direction parallel to the long axis of the transducer can be calculated. This velocity allows one to assess the degree of flow, such as blood flow. A typical display permits the quantitative analysis of velocities observed in a single anatomic location over time.

Color Doppler, on the other hand, is qualitative. It provides the location of detectable motion within the entire region of interest at one point. Red and blue are typically assigned to locations with frequency shifts that are either positive (motion towards the transducer) or negative (motion away from the transducer). While color Doppler is qualitative, it serves as a rapid survey of flow in the entire field. When quantitative measurements are required, color Doppler is often used first to guide the operator to the area of interest.

The ultrasound contrast medium used in the method of the invention may comprise any one of a large number of compounds or a mixture of these compounds, but must eventually decompose into innocuous materials when administered into an animal body.

The material properties of contrast media affect the resulting effectiveness of the evaluation. Typical important parameters include particle size, imaging frequency density, compressibility and particle behavior (surface tension, internal pressure, bubble-like qualities). Equally important are biodistribution characteristics and tolerance. Further, the transducer frequency, must be tuned to the medium used.

Typical ultrasound contrast media include bubbles in a physiologically acceptable liquid, protein-encapsulated bubbles, solid particles encapsulating a gas, polymers encapsulating a gas, lipids and liposomes encapsulating a gas, and fluorocarbon compositions. It is well known that gas is highly reflective within the vascular space and tissues. Free gas bubbles in a physiologically acceptable liquid, which range in size from about 2 $\mu$m to 12 $\mu$m and persist from 2 or 3 to 30 seconds, have been used, for example, to opacify cardiac chambers. While gas-based contrast media are extremely reflective and produce efficacious results at small dosages, they tend to be short-lived in animal plasma. Echogenicity may be as short as several seconds and tends to provide only first pass data. None usually pass the pulmonary capillaries to opacify, for example, the left ventricle of the heart.

Preferably, the contrast medium of the invention is persistent for more than a few circulation times and capable of reaching the placenta from the vascular tree into which it is injected. To increase the stability or longevity of the bubbles, gas can be encapsulated within a protective shell, usually a protein such as gelatin. Among the several types of encapsulated media, the human albumin microsphere, given the trade name Albunex ® (Molecular Biosystems, San Diego, Calif.) is often used for echocardiography. Also useful are galactose particles (8HU-454 ® and SHU-508 ®, Echovist ®, Schering AG, Berlin, Germany) with the gas being carried on the surface of the particle as an inside-out bubble, lipids (monolayer) encapsulating a gas, and liposomes (gas-filled lipid bilayer bubbles or microbubbles having a hydrophilic layer and an opposing hydrophobic layer).

Thus, by changing the chemical nature of the contrast medium, the ultrasound bloom duration can be increased to a longer periods of time. Certain contrast media persist longer, causing the bloom to be visible for a considerable length of time. Other contrast media, being quickly destroyed by the animal body, cause the bloom to fade more rapidly. Therefore, a balance must be struck so that the half life of the contrast medium is sufficient to permit satisfactory observation but not so long as to persist in the circulation of the subject. This is one of the important factors affecting the choice of an appropriate contrast medium for claimed invention. Preferably, the contrast medium is chosen to ensure a bloom having a predetermined, predictable lifetime, with a lifetime between about five seconds and about five minutes being particularly preferred.

Solid particles, e.g., of iodipamide ethyl ester, have been used to opacify internal organs. Solid particle formulations can exhibit reflectivity increased by as much as a factor of twenty by entrapping gas in the solid matrix. These formulations of solid particles encapsulating a gas show vascular and tissue enhancement from intravenous injections that may persist for as long as several minutes.

Successful and persistent tissue opacification from intravenous infusion has also been achieved by the use of fluorocarbon compositions, usually emulsions. Visualization of flow, tissue perfusion, and Doppler enhancement has also been achieved with fluorocarbon emulsions administered intravenously for example, with Fluosol ®, a 20% w/v emulsion of perfluorooctylbromide. While fluorocarbon emulsions are efficacious and produce a prolonged effect (sometimes for an hour or more) on vascular and tissue enhancement, they are less reflective than gases such as air and therefore require larger dosages to produce a comparable echogenic effect; also they may be too persistent. Encapsulated gas bubbles are most preferred, usually providing both stability and good echogenicity.

The reflectivity of particulate contrast media is also related to the particle's scattering cross-section, which in turn is related to particle size, the difference in the acoustic impedance of the medium and the surrounding environment, particle elasticity, and the frequency of the interrogating sound wave from the transducer.

Of the above-listed factors, particle size has the most profound effect on reflectivity. Specifically, the amount of backscatter is related to $r^6$, where r is the radius of the particle. However, particle size must be very small to successfully traverse the capillary bed. Preferably, the particle size of the contrast medium is less than or equal to about 8 $\mu$m, more preferably less than 7 $\mu$m, such that it is small enough to pass through the capillary bed.

Both the particle size and the bulk properties of the medium (acoustic impedance) greatly affect the scattering cross-section of the particle. For instance, perfluorochemicals, solid particles, and air bubbles are 7, 10, or even $10^{10}$ times more reflective than red blood cells respectively.

Further, the elasticity of the particle, which is related to the compressibility of the medium and the stiffness of the outer shell of the particle, can dramatically affect reflectivity, allowing a particle with a small diameter (less than 5 $\mu$m) to increase in scattering cross-section a few orders of magnitude to become effective at commonly used clinical frequencies with a wavelength on the order of 200–500 $\mu$m. Gas, and to a much lesser degree fluorocarbons, are compressible and can potentially exhibit a resonance phenomenon.

Other specific characteristics that may be important in the selection of one or more appropriate contrast media include the distribution of bubbles or particles in comparison to the distribution of echoes, signal-to-noise ratio, and special characteristics of the echoes of the uterus, placenta, umbilical cord and fetal tissue.

The contrast media of the invention may include ultrastable microbubbles, which can now be manufactured in a tight range of diameters (such as 1–5 $\mu$m) with a mean diameter of about 2$\mu$m. These media can enhance the echogenicity of these tumors for at least up to 5 minutes. This medium is described by Simon in an article entitled "Quantitative Assessment of Tumor Enhancement by Ultrastable Lipid-Coated Microbubbles as a Sonographic Contrast Agent" in *Inves Radiol* (1992) 27:29–34 (1992).

Thus, the chemical nature of the contrast medium should be such that there is minimal impact on the mother and the fetus, but provision of the desired degree of bloom and duration of bloom upon visual inspection of the ultrasound imaging output.

A wide variety of contrast media is available commercially. These media include fluorocarbon-based formulations Imagent US TM (Alliance Pharmaceutical) and Echogen TM (Sonus Pharmaceutical); cellulose or other carbohydrate formulations such as $SonoR_x$ TM ($ImaR_x$ Pharmaceutical) MB-U820 TM (Molecular Biosystems), Echovist TM and Levovist TM (Schwing AG), liposomal compositions such as Aerosomes TM ($ImaR_x$ TM ) and Filmix TM (Cavcon); protein microspheres such as Albunex TM (Molecular Biosystems) and iodinated polymeric microparticles called "bubbles" (Medicprise LP). The choice of suitable contrast medium is governed by the principles set forth above.

One or more contrast media can be administered. The media may be administered as such or coupled to a targeting compound, such as a monoclonal antibody or peptide, that is able to attach to a surface protein specific to the maternal placenta.

The contrast medium can be administered by injection into the maternal circulatory system, for example, in arteries or veins or by any other mode that selectively targets the maternal placenta. Alternatively, the contrast medium can be instilled into the amniotic cavity or injected directly into the fetal circulation, for example, by fetal cordo-infusion.

The amount of the contrast agent administered can vary widely, depending on the type of contrast agent used, the route of administration, the desired bloom intensity or duration, and the possibility of any adverse effects to the mother or fetus. Typically, the dosage level is somewhere in the range of about 0.5 to about 20 cc/kg, preferably about 0.1 to about 10 cc/kg, most preferably from about 0.2 to about 5 cc/kg.

The claimed invention allows direct visualization of movement in the arcuate arteries, spiral arteries and intervillous space, thus ascertaining the level of maternal blood flow into the placenta and evaluating whether the pregnancy is progressing normally. Previously, this aspect of maternal circulation has not been visible without the need to interfere with fetal circulation.

Further, when high quality visual images representing the ultrasound information are captured on high quality VHS video recording tape, subsequent video-densitometry analysis can be performed. An initial densitometric analysis of the placental flow can provide a time-intensity curve, which has potential to quantify the wash-out characteristics of the contrast medium. For example, FIGURE 1 demonstrates graphically the change in intensity versus time for two different compositions. "Density—E" in FIGURE 1 identifies the time intensity curve for the contrast medium galactose particles (sold by Schering AG, Berlin, Germany under the trade name Echovist ®). "Density—S" in FIGURE 1 identifies the time intensity curve for agitated saline.

Using one aspect of the claimed method, by recording the increase in perceptible blood flow after the injection of a standard contrast medium followed by its fading away, a graphic representation of "normal" placental blood flow activity can be established. Thus, by manipulating the chemical nature of the contrast medium to produce a "standard" time-intensity curve, "normal" placentation can be better understood and defined in terms of the minimally acceptable volume and velocity of maternal blood flow. Time-intensity curves which deviate significantly from the norm can then be used to identify a placenta with abnormalities or meaningful pathologies.

For example, when significant abnormalities are present, one may not be able to achieve as intense a bloom peak, or to achieve a bloom peak in the usual time, perhaps not at all. Alternatively, a prolonged fade period may be a key characteristic of normal, healthy placentas. Thus, useful parameters that can for the first time be quantified reliably using the claimed method include peak intensity, the area under the time-intensity curve, bloom half-life, and other measurements arising from various types of algorithmic analyses.

Therefore, the claimed invention provides a method for characterizing what "normal" placentation means and defining various pathological conditions in terms of measurable parameters. Further, this method of identifying placenta pathologies can be used to intervene with therapeutic treatment, if necessary, at an earlier time when treatment is likely to be more meaningful. For example, appropriate responses to a time-intensity curve exhibiting significant abnormalities might indicate that the mother's behavior should be modified to optimize blood flow to the placenta, for example, restrictions in the level of the mother's physical activities or nutritional habits.

The invention will be further clarified by the following example, which are intended to be purely illustrative of the invention.

EXAMPLE 1

Contrast Ultrasonography of Uteroplacental Blood Flow

A study of nine pregnant female baboons was performed under medical and veterinary supervision. The baboons (P. cynocephalus) were each in the range of 6-12 years of age and each weighed in the range of 15-18 Kg.

At 89 to 137 days of gestation, the pregnant baboons were each immobilized and maintained with 15 mg/kg of ketamine hydrochloride IM (sold by Parke-Davis under the trade name Ketalar ®). Adequate tranquilization was provided for performing the sonography and to assure adequate blood pressure monitoring. A catheter was inserted into any accessible vein of each animal to collect blood for CBC and clinical chemistry. About 0.25 mg/kg of diazepam (sold by Roche Products under the trade name Valium ® IV) was injected, with exact doses varying as needed to keep the animal tranquilized and to establish baseline measurements. After an 18 gauge catheter was then inserted percutaneously into either the left or right femoral artery for blood gas sampling and monitoring, the blood pressure and pulse oximetry monitoring was begun.

Prior and subsequent to injection of contrast media, a complete fetal biophysical profile was obtained. The contrast media were injected arterially or intravenously followed by a 5 cc saline flush. The contrast medium was injected while monitoring fetal EKG and separate, but simultaneous, ultrasound assessment of the arterial cardiac chamber.

2-D gray-scale ultrasound and color Doppler were used to study uteroplacental and intervillous blood flow as follows. The ultrasound transducer was fixed on the animal's abdomen and focused on either a full cross-section of the placenta or an individual cotyledon (a section of the placenta). Once in a steady state, the gain of the transducer was then reduced to produce a low intensity signal, so that very little Doppler or color Doppler activity could be seen on the CRT visual display connected via a computer to the transducer.

When the contrast medium was introduced, the flushing of the medium through the placenta could be observed as a lighting up of the intervillous space to form a "bloom." The bloom caused by the medium then faded away as the medium was washed out of the intervillous space. Various types of contrast media and degassed saline (control) were injected into the femoral arteries of the various animals tested, as needed. Ultrasound studies were repeated after each injection at standardized intervals.

The contrast media tested were lipid coated microspheres (Filmix-Vet ®), nitrogen-filled liposomes (Aerosomes ®), galactose-encapsulated gas-filled bubbles (Echovist ®), and agitated saline, with de-gassed saline being used as a control (no contrast medium). A summary of the gestation periods of the different animals and the various contrast media used with each is shown below:

TABLE 1

| Animal | Gestation | Medium | Dose | Comments |
|---|---|---|---|---|
| A | 137 (78%) | Aerosomes ® | 0.3 cc/kg<br>0.6 cc/kg<br>0.6 cc/kg | —;<br>—;<br>—. |
| B | 136 (78%) | Aerosomes ® | 0.6 cc/kg<br>1.1 cc/kg | —;<br>color image. |
| C | 132 (75%) | Filmix-Vet ® | 0.3 cc/kg<br>1.2 cc/kg | —;<br>Placental ring. |
| D | 132 (75%) | Filmix-Vet ® | 0.6 cc/kg<br>1.2 cc/kg | Placental ring;<br>—. |
| E | 137 (78%) | Echovist ® | 5 × 2 cc | Intra-arterial. |
| F | 132 (75%) | Echovist ® | 5 × 2 cc | Intra-arterial. |
| G | 109 (62%) | Saline<br>Echovist ® | 2 cc<br>5 × 2 cc | 6 days behind in growth;<br>Intra-arterial. |
| H | 89 (51%) | Aerosomes ® | 0.6 cc/kg<br>0.6 cc/kg | —;<br>—. |
| I | 89 (51%) | Aerosomes ® | 0.9 cc/kg<br>0.2 cc/kg | Hand held (arcuate artery);<br>Kidney and heart images. |

The parameters measured, both with and without contrast media, included subjective enhancement of 2-D, gray-scale Doppler and color Doppler flow images. The study compared basal state subjective (see comments in Table 1) and objective ultrasound/Doppler information for each of the injected substances.

In the gray-scale mode, immediately after injecting the contrast medium, actual particulates were observed moving in the direction of the blood flow. In the color mode, the bloom was exhibited on a color CRT monitor as increased color activity in that area, with different colors indicating various blood velocities.

Maternal and fetal effects (cardiopulmonary parameters) of the injections were also monitored, with fetal well-being being assessed throughout the procedure. The following were monitored:

For Placental Stroma (Intervillous Space)

2-D gray-scale (lower magnification, full placental ring), both Static and Real time; 2-D RES (Region Expansion Selection, section of placenta, e.g., a cotyledon of the placenta or a portion thereof), both Static and Real time; Standard Color with Variance Map;

For Myometrium and Arcuate Artery

2-D gray-scale, both Static and Real time; 2-D RES, both Static and Real time; Standard Color with Variance Map;

The Following Vital Signs were Monitored

Blood Pressure, Heart Rate, Respiration Rate, and Arterial Blood Gases.

By visual inspection of the images produced by gray scale or color Doppler, the results showed the appearance of the bloom when contrast media were added. In addition, all studies were recorded on high-resolution video tape for more detailed analysis.

The results showed that, once the gain was properly adjusted, most of the ultrasound contrast media tested could be used successfully to augment sonographic examination of the placenta in pregnant animals, even enabling the visualization of the maternal blood flow through the intervillous space of the placenta. Further, none of the animals or their fetuses appeared to suffer any adverse effects, either at the immediate conclusion of the test or one week later when biophysical profiles were again performed for three of the animals. Therefore, it was concluded that uteroplacental blood flow could be evaluated during pregnancy, thus enabling the possibility for early therapeutic intervention.

I claim:

1. A method for evaluating blood flow in the placenta of a pregnant, female animal comprising the steps of:
   a. administering to the animal an effective amount of a contrast medium;
   b. observing the flushing of said contrast medium through the placenta by scanning the abdomen of the animal with the transducer of an ultrasound scanner, thereby obtaining a scan; and
   c. assessing the condition of the placenta by evaluating the scan.

2. The method of claim 1 wherein the condition of the intervillous space on the placenta is evaluated.

3. The method of claim 1 wherein the rate and direction of blood flow through the intervillous space on the placenta is evaluated.

4. The method of claim 1 wherein the contrast medium is selected from the group consisting of bubbles in a physiologically acceptable liquid, protein-encapsulated bubbles, solid particles encapsulating a gas, polymers encapsulating a gas, lipids and liposomes encapsulating a gas, and fluorocarbon compositions.

5. The method of claim 1 wherein the contrast medium is coupled to a monoclonal antibody or a peptide.

6. The method of claim 1 wherein the contrast medium is a liposome encapsulating a gas microbubble.

7. The method of claim 1 wherein a 2-D ultrasound image of the placenta is generated.

8. The method of claim 1 wherein a gray-scale Doppler image of the placenta is generated.

9. The method of claim 1 wherein a color Doppler image of the placenta is generated.

10. The method of claim 1 further comprising the step of generating a time-intensity curve.

11. The method of claim 1 wherein the particle size of the contrast medium is less than about 7 $\mu$m.

12. The method of claim 1 wherein said administering is by injection into maternal circulation.

13. The method of claim 1 wherein said administering is by instillation into the amniotic cavity.

14. The method of claim 1 wherein said administering is by direct injection into the fetal circulation.

* * * * *